United States Patent [19]

Carenzi et al.

[11] Patent Number: 4,766,138
[45] Date of Patent: Aug. 23, 1988

[54] USE OF 4-(ISOXAZOLYL)-THIAZOLE-2-OXAMIC ACID DERIVATIVES

[75] Inventors: Angelo Carenzi, Busto Arsizio; Dario Chiarino, Monza; Davide Della Bella, Milan; Giancarlo Grancini, Nova Milanese, all of Italy

[73] Assignee: Zambon S.p.A., Vicenza, Italy

[21] Appl. No.: 849,458

[22] PCT Filed: Jul. 30, 1985

[86] PCT No.: PCT/EP85/00380
 § 371 Date: Mar. 13, 1986
 § 102(e) Date: Mar. 13, 1986

[87] PCT Pub. No.: WO86/00899
 PCT Pub. Date: Feb. 13, 1986

[30] Foreign Application Priority Data

Jul. 31, 1984 [IT] Italy ............................... 22150 A/84

[51] Int. Cl.$^4$ ................. C07D 417/04; A61K 31/425
[52] U.S. Cl. ..................................... 514/371; 548/195; 548/197
[58] Field of Search ................. 548/195, 197; 514/371

[56] References Cited

U.S. PATENT DOCUMENTS 4,246,271  1/1981  Cousse ............................... 548/195

Primary Examiner—Robert Gerstl
Attorney, Agent, or Firm—Stevens, Davis, Miller & Mosher

[57] ABSTRACT

Use of 4-(isoxazolyl)-thiazole-2-oxamic acid derivatives; method for preparing them and intermediate compounds useful for their preparation.

Said compounds possess antiarthritic activity; compositions for pharmaceutical use containing said compounds as the active ingredients are also described.

7 Claims, No Drawings

USE OF 4-(ISOXAZOLYL)-THIAZOLE-2-OXAMIC ACID DERIVATIVES

This invention relates to the use of 4-(isoxazolyl)-thiazol-2-oxamic acid derivatives as antiarthritic agents, their preparation, pharmaceutical composition containing them, and new 4-(isoxazolyl)-thiazole compounds.

More particularly, this invention relates to the use of the compounds of formula:

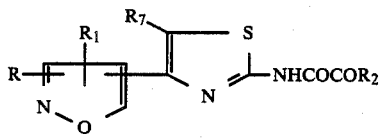

wherein

R and $R_1$ which may be the same or different represent a hydroxy group; a hydrogen or halogen atom; a $C_1$–$C_6$ alkyl or alkoxy group optionally substituted by from one to three substituents selected from the group consisting of halogen, hydroxy, alkoxy, amino, carboxy, alkoxycarbonyl, alkoxalyloxy and phenyl, the latter in turn optionally substituted by from one to three substituents selected from the group consisting of halogen, hydroxy, alkoxy, amino and trifluoroalkyl; a phenyl group optionally substituted by from one to three substituents selected from the group consisting of halogen, hydroxy, alkoxy, amino and trifluoromethyl;

$R_2$ is a hydroxy group, an $OR_3$ group or an $NR_4R_5$ group;

$R_3$ is a $C_1$–$C_6$ alkyl group optionally substituted with from one to three substituents selected from the group consisting of hydroxy, alkoxy, amino, carboxy and alkoxycarbonyl; a $C_{5-6}$ cycloalkyl group optionally substituted by from one to three alkyl groups; a $C_7$–$C_9$ phenylalkyl group optionally substituted on the phenyl ring by from one to three substituents selected from the group consisting of halogen, methyl and methoxy group; a group of the formula —$(CH_2$—$CH_2$—$O)_n$—$R_6$ wherein n is an integer number from 2 to 4 and $R_6$ is a hydrogen atom or an alkyl group; $R_4$ and $R_5$ which may be the same or different are a hydrogen atom, an alkyl, a $C_5$–$C_6$ cycloalkyl, a $C_7$–$C_9$ phenylalkyl, or a phenyl group; or $R_4$ and $R_5$ together with the nitrogen atom to which they are linked, form a 1-piperidyl, 1-piperazinyl, 4-methyl-1-piperazinyl, pirazolyl, thiazolyl or imidazolyl radical; or either $R_4$ or $R_5$ is a hydrogen atom and the other a group of the formula

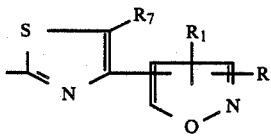

wherein

R and $R_1$ have the above indicated meanings.

$R_7$ is a hydrogen atom or a $C_1$–$C_3$ alkyl radical.

Another object of this invention is the use of the salts of the compounds of formula I in which $R_2$ is a hydroxy group with pharmaceutically acceptable organic and inorganic bases and the salts of the compounds of formula I in which $R_2$ contains a basic function with pharmaceutically acceptable organic and inorganic acids.

If not otherwise specified alkyl means a straight or branched $C_1$–$C_4$ alkyl group;

alkoxy means a $C_1$–$C_4$ alkoxy group;

alkoxycarbonyl means an alkoxycarbonyl group having from 1 to 4 carbon atoms in the alkoxy moiety;

halogen means fluorine, chlorine, bromine or iodine atom.

Depending on the meaning of the substituents, some of the compounds of formula I can exist in the form of isomers.

It is an object of this present invention either the use of the isomer mixtures or of the single isomers obtained by separation from the mixture or by stereospecific synthesis.

Examples of compounds included in formula I are the following

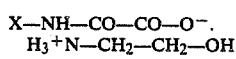

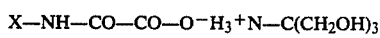

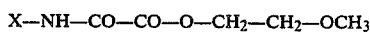

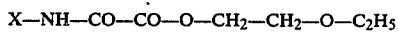

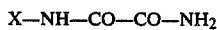

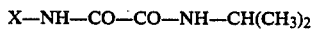

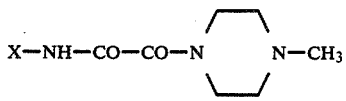

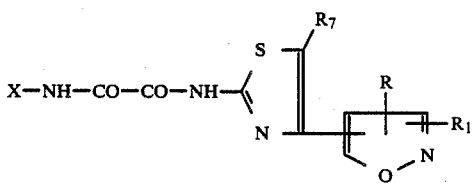

wherein X is the group

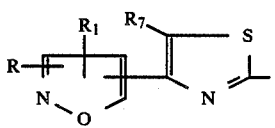

wherein R, $R_1$ and $R_7$ have the same meaning as set forth above.

Typical examples of R and $R_1$ include fluorine, chlorine, bromine, iodine, propoxycarbonyl, ethoxycarbonyl, methoxycarbonyl, methyl, ethyl, propyl, isopropyl, hydroxypropyl, hydroxyethyl, hydroxymethyl, propyloxypropyl, propyloxymethyl, methyloxyethyl, metoxymethyl, ethoxymethyl, ethoxalyloxypropyl (—$C_3H_6OCOCOOC_2H_5$), propoxalyloxymethyl (—$CH_2OCOCOOC_3H_7$), ethoxalyloxymethyl (—$CH_2OCOCOOC_2H_5$), 2-bromophenyl, 2-iodophenyl, 2-chlorophenyl, 2,6-dichlorophenyl, 2-chloro-6- fluorophenyl, methoxy, ethoxy, propoxy, phenylethoxy and benzyloxy.

Preferred meanings of R and $R_1$ are hydrogen, chlorine, bromine, hydroxy, methyl, methoxy, ethoxy, benzyloxy, phenyl, halosubstituted phenyl hydroxymethyl, methoxymethyl, ethoxalyloxymethyl and carbethoxy.

The compounds of formula (I) are valuable immunodepressive agents in mammals.

For example, the esters of formula I ($R_2=OR_3$) may also be prepared by transesterification or other esters of formula I, or by reacting an acyl halide of an acid of formula I ($R_2=OH$) with the suitable alcohol of formula $R_3$-OH.

Similarly, the compounds of formula

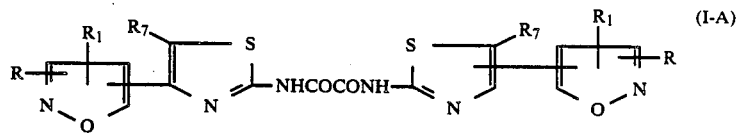

A further object of this invention are the compounds of formula (I) except when $R_2$ is hydroxy or $OR_3$ and the isoxazolyl radical is a 3- or a 5-isoxazolyl radical.

Preparation of the compounds of formula I is performed according to procedures known in organic chemistry and is accomplished through the reactions set forth in scheme 1 below

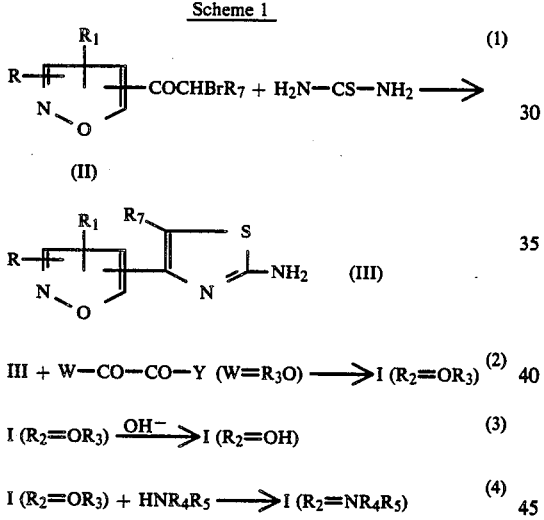

($R$, $R_1$, $R_2$, $R_3$, $R_4$, $R_5$ and $R_7$ have the meanings set forth in connection with general formula I; Y is chlorine or bromine; W is chlorine, bromine or $R_3O$)

The bromoacetyl-isoxazole derivative (formula II) is condensed (reaction 1, scheme 1) with thiourea to give a derivative of 2-amino-4-isoxazolyl-thiazole (formula III).

Condensation is performed by heating the mixture of reactants in a protic or aprotic polar solvent at a temperature preferably between 50° C. and 100° C.

The compond of formula III is then reacted (reaction 2) with a halide of oxalic acid monoester obtaining the compounds of formula I wherein $R_2$ is an $OR_3$ group.

Reaction 2 is performed preferably in pyridine or in an inert solvent in the presence of an acid-acceptor.

From the compounds of formula I wherein $R_2=OR_3$ are prepared by reaction with an aqueous inorganic base (reaction 3) the free acids (I, $R_2=OH$) and with an organic base of formula $HNR_4R_5$ (reaction 4) the compounds of formula I wherein $R_2=NR_4R_5$.

As appears evident to persons skilled in the art, the compounds of this invention may be prepared by alternative procedures with respect to those set forth in scheme 1.

are normally prepared according to the reactions of scheme 1 but, in the case where the two pairs of substituents R and $R_1$ are identical, they can also be prepared by condensing 2 moles of the suitable compound of formula III with oxalyl dihalide (W—CO—CO—Y; W=Y=halide)

Compounds of formula I in the form of salts are prepared by reacting a compound of formula I wherein $R_2=OH$ with a pharmaceutically acceptable organic or inorganic base.

Similarly, the salts may be also prepared by reacting a compound of formula I wherein $R_2$ contains a basic function (e.g. $R_2=$4-methyl-1-piperidinyl) with a pharmaceutically acceptable organic or inorganic acid.

The compounds of formula II are in part compounds known as such or at the precursor level.

In any case, they are prepared by known techniques.

An example of synthesis is given in scheme 2.

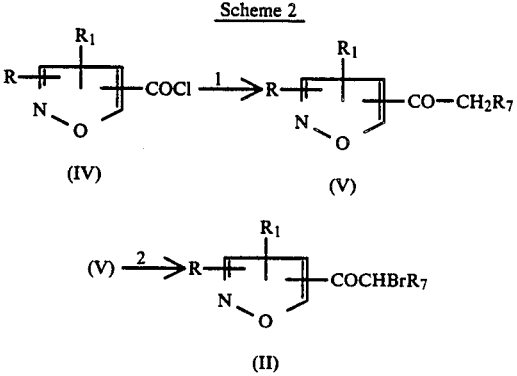

Reaction 1 of Scheme 2 is performed by reacting an acyl chloride IV with diethylmalonate or a diethylalkylmalonate and carbon tetrachloride in the presenc of magnesium, according to known techniques.

Reaction 2 of scheme 2 is performed by brominating an intermediate V with pyridine perbromide hydrobromide or other brominating agents in solvents such as carbon tetrachloride, chloroform, methyl chloride, etc.

Among the known compounds of formulas V and II may be mentioned 3-bromo-5-acetyl-isoxazole (European Pat. No. 16,255), 3-methoxy-5-acetyl-isoxazole (Acta Chem. Scan., B, 28, 639, 1974), 3-bromo-5-bromoacetyl-isoxazole (European Pat. No. 16,255), 4-acetyl-3-phenyl-5-methylisoxazole (Gazz. Chim. It., 76, 200, 1946), 4-acetyl-3-(2-chlorophenyl)-5-methylisoxazole (Nippon Kagaku Z., 92, 639, 1971), 3-bromoacetyl-5-phenyl-isoxazole (J. Med. Chem., 10, 411, 1967)

The compounds of formula III are new when the isoxazolyl group is a 4-isoxazolyl radical and are a further object of this invention.

The pharmacological investigation proved that the compounds of this invention possess interesting antiarthritic properties.

Antiarthritic activity was appraised using the test for Freund experimental arthritis induced in the rat by a subplantar injection of a 0.5% solution of killed Butyricum mycobacteria in parrafin oil as described by Newbould B. B. (Brit. J. Pharmacol., 1963, 21, 127).

Compounds found to be active in Freund's experimental arthritis were shown to have considerable clinical usefulness in the treatment of rheumatoid arthritis.

The therapy of rheumatoid arthritis, a disease of the connective tissues with unclear aetiology, provides for the employment mainly of drugs belonging to two classes: nonsteroid and immunodepressive antiphlogistic agents.

The experimental model of Freund's arthritis used for the pharmacological investigation of the compounds of this invention makes it possible not only to appraise pharmacological activity but to acquire sound indications on the mechanism of the action of the tested compounds.

In this experimental model the drugs with antiinflammatory activity are more effective in the stage sustained predominantly by a specific inflammatory mechanism (primary stage), while the drugs with immunodepressive activity are more effective in the stage sustained principally by an immunity mechanism (secondary stage).

The pharmacological investigation of the compounds of this invention was conducted by administering to the experimental animal dosage levels of from 20 to 40 mg/kg/day for a period of 28 consecutive days beginning the day before innoculation of the mycobacteria.

Pharmacological activity was measured by determining both the velocity of erythrosedimentation (VES) and change in volume of the hind limbs.

The limb which was the seat of the innoculation represents the primary stage while the contra-lateral limb, where the onset of the pathological process takes place about the 12th day after innoculation, represents the secondary stage.

Treatment of the mycobacteria-innoculated animals with N-[4-(3-bromo-5-isoxazolyl)-2-thiazolyl]-oxamide brought the VES index almost to normalization in 40% of the animals when 40 mg/kg were administered orally and in 70% of the animals when 20 mg/kg were injected peritoneally.

The peritoneal treatment also led to a 60% inhibition of volume growth in the contra-lateral limb (secondary stage).

Treatment of the animals with N,N'-bis-[4-(3-bromo-5-isoxazolyl)-2-thiazolyl]-oxamide (35 mg/kg peritoneally) led to maintenance of the VES around the values exhibited by the group of animals not innoculated with mycobacteria, i.e. 100% protection.

As regards the increase in volume of the contra-lateral limb, peritoneal administration of 35 mg/kg of N,N'-bis-[4-(3-bromo-5-isoxazolyl)-2-thiazolyl]-oxamide gave 70% increase protection.

The compounds investigated did not show any significant effect on the inflammatory development stage of experimental arthritis.

Systemic tolerability of the compounds proved very favourable. From the tests conducted in the experimental animal no toxic phenomena appeared with 0.5 g/kg doses in parenteral administration and 1.5 g/kg with oral treatment. The ratio of the effective pharmacological dose to the tolerated dose proved very favourable.

The therapeutical indications of the compounds in question are represented by the different syndromes which accompany the arthritic and rheumatic processes.

The therapeutic dosage ranges from 5 to 500 mg/day.

The compounds of this invention are useful for treating the various syndromes which accompany the arthritic and rheumatic processes.

Another object of the present invention are the pharmaceutical compositions containing as active ingredient the compounds of formula (I) or their pharmaceutically acceptable salts.

These compositions can contain the active ingredient together with pharmaceutically acceptable organic or inorganic solid or liquid excipients and can be suitable for topical, oral, parenteral, or rectal administration.

The finished pharmaceutical preparations can be solid, such as for example tablets, pills, capsules, powders, granules, suppositories; or liquid such as for example solutions, suspensions, emulsions, or semiliquids such as creams and ointments. They can even be prepared in such a manner that the release of the drug is prolonged after administration.

In addition to the excipients they can contain preservative, stabilizing, wetting and emulsifying agents, salts to regulate osmotic pressure, buffers, colourings, flavourings, etc.

They can be prepared according to known methods and can also contain other therapeutic ingredients.

In order to better illustrate the present invention the following examples are now given.

EXAMPLE A

1-[3-(2-chloro-6-fluorophenyl)-5-isoxazolyl]-ethanol 27.60 g (273 mmol) of triethylamine were added dropwise to a solution of 28.4 g (136.5 mmol) of alpha, 2-dichloro-6-fluorobenzaldoxime and 19.14 g (273 mmol) of 3-butin-2-ole in 250 ml of benzene kept under stirring at 8°–10° C.

When the addition was over the mixture was heated to 60° C.; after 1 hour the mixture was cooled and extracted with 10% hydrochloric acid and then with water.

Evaporation of the organic phase gave 31.1 g of an oil which was purified by distillation and the fraction boiling at 140°–150° C. (0.3 mmHg) was collected. 1HNMR (CDCl$_3$): delta 7.6–7 (m, 3H); 6.4 (s, 1H); 5.1 (q, 1H); 1.6 (t, 3H).

EXAMPLE B (1) 3-(2-chloro-6-fluorophenyl)-5-acetylisoxazole

To a solution of 30 g (124 mmol) of 1-[3-(2-chloro-6-fluorophenyl)-5-isoxazolyl]-ethanol in 187 ml of acetic acid maintained under stirring at 5° C. were added dropwise 9.07 g (90.7 mmol) of CrO$_3$ in 9.34 g of water and 132 ml of acetic acid.

The mixture was kept overnight under stirring at room temperature; the solvent was then removed by evaporation and the residue was taken up with water, made neutral with sodium bicarbonate and extracted with ethyl ether.

The ethereal extracts were combined and washed with water, dried and evaporated to dryness; 27.8 g of an orange oily product were obtained. The oil was distilled under reduced pressure and the fraction boiling at 120°–122° C. (0.4 mmHg) was collected; yield, 23.7 g.

The oil was allowed to crystallize by standing and then recrystallized from isopropyl ether; m.p. 46°–47° C. 1HNMR (DMSO): delta 7.9–7.3 (m, 4H); 2.8 (s, 3H).

In a similar manner were obtained:

3-carbethoxy-5-acetylisoxazole, Yield, 82%; m.p. 67°–68° C. (isopropyl ether); 1HNMR (CDCl$_3$): delta 7.3 (s, 1H); 4.5 (q, 2H); 2.7 (s, 3H); 1.5 (t, 3H).

The starting compound, i.e. 1-(3-carbethoxy-5-isoxazolyl)-ethanol, was prepared according to European Pat. No. 28,355.

3-methoxymethyl-5-acetylisoxazole, Yield, 58.5%; colourless oil, b.p. 72°–74° C. (0.4 mmHg); 1HNMR (CDCl$_3$): delta 7.0 (s, 1H); 4.6 (s, 2H); 3.4 (s, 3H); 2.6 (s, 3H).

The starting compound, i.e. 1-(3-methoxymethyl-5-isoxazolyl)-ethanol, was prepared according to German Pat. No. 2,754,832.

(2) 3-benzyloxy-5-acetylisoxazole 2.2 g (90.5 mmol) of magnesium turnings were added under stirring to a solution of 14 g (87 mmol) of diethyl malonate in 78 ml of ethyl ether containing 63 g of anhydrous ethyl alcohol and 0.90 ml of carbonium tetrachloride.

The mixture was refluxed for 2 hours and then was added dropwise a solution of 18.8 g (79 mmol) of 3-benzyloxy-5-isoxazolylcarbonyl chloride (Belgian Pat. No. 665,249) in 65 ml of ethyl ether.

The mixture was refluxed for 2 hours, cooled to room temperature and 159 ml of 2M sulfuric acid were added.

After vigorous stirring, the organic layer was separated, washed with water and evaporated to dryness.

The thus obtained oily residue (29.9 g) was added to a solution of 4.8 g of concentrate sulfuric acid in 36.3 ml of acetic acid and 25 ml of water; the mixture was refluxed for 8 hours.

The mixture was cooled to 20° C. and made neutral (pH 6.5) with 10M potassium hydroxide at constant temperature.

The mixture was extracted with chloroform; the combined organic extracts were evaporated to give an oily residue which was taken up with 150 ml of hexane. The crystalline precipitate was collected by filtration (6.7 g; Yield, 39%) and recrystallized from isopropyl ether. m.p. 77°–78° C. 1HNMR (CDCl$_3$): delta 7.5 (m, 5H); 7.2 (s, 1H); 5.4 (s, 2H); 2.5 (s, 3H).

(3) 3-(2-chloro-6-fluorophenyl)-5-methyl-4-acetylisoxazole

To a solution of 2.3 g (100 mmol) of sodium in 220 ml of anhydrous ethanol were added 10 g (100 mmol) of acetyl acetone.

The reaction mixture was cooled to 0° C. and 17 g (81.6 mmol) of alpha, 2-chloro-6-fluorobenzaloxime (German Patent Application No. 2,323,809) were added dropwise while stirring vigorously and maintaining the temperature at about 5° C.

The mixture was stirred overnight at room temperature and then made neutral with 10% hydrochloric acid. The mixture was concentrated to dryness and the residue was taken up with 100 ml of water and 150 ml of ethyl ether.

The organic layer was separated, washed with dilute sodium hydroxide and then with water till neutral.

The solvent was removed by evaporation and the oily residue distilled under reduced pressure; p.b. 129°–131° C. (0.5 mmHg); Yield, 14.5 g (70%) of a clear colourless oil. 1HNMR (CDCl$_3$): delta 7.9–7.3 (m, 3H), 2.8 (s, 3H), 2.3 (s, 3H).

EXAMPLE C (1) 3-chloro-5-bromoacetylisoxazole 28.65 g (179 mmol) of bromine in 20 ml of chloroform were added dropwise in 10 minutes to a solution of 25 g (172 mmol) of 3-chloro-5-acetylisoxazole containing 4.9 ml of glacial acetic acid while the reaction mixture was maintained under stirring at 48°–50° C.

After 5 minutes the mixture was poured into 300 g of water and crushed ice.

The organic layer was separated, washed with water, dried and evaporated to residual.

Yield, 37 g (96%) of an oily compound which can be purified by distillation; b.p. 97°–99° C. (2 mmHg). 1HNMR (CDCl$_3$): delta 7.00 (s, 1H), 4.37 (s, 2H).

In a similar manner were prepared the following compounds:

3-methoxy-5-bromoacetylisoxazole, (from 3-methoxy-5-acetyl-isoxazole, Acta Chem. Scand. 28 B, 639, 1947); Yield, 91%; deliquescent crystalline compound; 1HNMR (CDCl$_3$): delta 6.63 (s 1H); 4.33 (s, 2H); 4.00 (s, 3H).

3-benxyloxy-5-bromoacetylisoxazole, Yield, 83%; white crystalline compound, m.p. 80°–81° C. (isopropyl ether); 1HNMR (DMSO-d$_6$): delta 7.37 (s, 5H), 7,29 (s, 1H), 5.28 (s, 2H), 4.71 (s, 2H).

3-phenyl-5-methyl-4-bromoacetylisoxazole, (from 3-phenyl-5-methyl-4-acetylisoxazole, Gazz. Chim. It. 76, 200, 1946); Yield, 87%; white crystalline compound, m.p. 46°–48° C. (isopropyl ether); 1HNMR (CDCl$_3$): delta 7.57 (m, 5H), 3,22 (s, 2H), 2.71 (s, 3H).

5-hydroxymethyl-3-bromoacetylisoxazole, (from 5-hydroxylethyl-3-acetylisoxazole, II Farmaco, Ed. sci, 39, 487, 1984); Yield 94%; oily compound, b.p. 160° C./0.3 mmHg, 1HNMR (CDCl$_3$): delta 6.72 (s, 1H), 4.85 (s, 2H), 4.60 (s, 2H).

3-methyl-5-bromoacetylisoxazole, (from 3-methyl-5-acetylisoxazole, Gass. Chim. Ital. 72, 242, 1942); Yield, 87%; white crystalline compound, m.p. 44°–46° C. (isopropyl ether); 1HNMR (CDCl$_3$): delta 7.00 (s, 1H), 4.42 (s, 2H), 2.43 (s, 3H).

3-(2-chloro-6-fluorophenyl)-5-bromoacetylisoxazole, Yield, 85%; oily compound, b.p. 145°–150° C./0.3 mmHg; 1HNMR (CDCl$_3$): delta 7.8–7 (m, 4H), 4.60 (s, 2H).

3-carbethoxy-5-bromoacetylisoxazole, Yield, 83%; white crystalline compound, m.p. 74°–75° C. (isopropyl ether); 1HNMR (CDCl$_3$): delta 7.5 (s, 1H), 4.52 (q, 2H), 4.50 (s, 2H), 1.5 (t, 3H).

3-methoxymethyl-5-bromoacetylisoxazole, (from 3-methoxy-5-acetylisoxazole, Acta Chem. Scand. 28 B, 639, 1947); yield, 91%; oily compound. 1HNMR (CDCl$_3$): delta 7.1 (s, 1H), 4.4 (s, 2H), 3.4 (s, 3H).

1-(3-bromo-5-isossalolyl)-2-bromo-1-butanone, Yield, 98%; white crystalline compound, m.p. 53°–54° C. (hexane). 1HNMR (CDCl$_3$): delta 7.2 (s, 1H), 5.0 (t, 1H), 2.2 (m, 4H), 1.1 (t, 3H).

3-(2-chloro-6-fluorophenyl)-5-methyl-4-bromoacetylisoxazole, Yield, 86%; white crystalline compound, m.p. 74°–75° C. (isopropyl ether). 1HNMR (CDCl$_3$): delta 7.88–7.10 (m, 3H), 3.80 (s, 2H) 2.84 (s, 3H).

EXAMPLE D (1) 2-amino-4-(3-bromo-5-isoxazolyl)-thiazole

A mixture of 32.4 g (120.4 mmol) of 5-bromoacetyl-3-bromoisoxazole and 18.4 g (240 mmol) of thiourea in 400 ml of anhydrous ethanol was refluxed for 90 minutes.

The solvent was removed by distillation and the residue was taken up while stirring with 750 ml of ethyl ether and 160 ml of 10% aqueous potassium hydroxide. The ethereal extract was separated and washed with 50 ml of ethyl ether.

The extracts and the ethereal washings were combined and washed with water till neutral, dried over sodium sulfate and then evaporated to dryness.

The crystalline residue (28.7 g; 97%) was purified by recrystallization from methanol, m.p. 160°–162° C.; 1HNMR (DMSO-d$_6$): delta 7.47 (s, 1H); 6.97 (s, 1H).

In a similar manner were prepared the following compounds:

2-amino-4-[3-(2-chloro-6-fluorophenyl)-5-methyl-4-isoxazolyl]-thiazole, Yield, 81.5%; crystalline compound, m.p. 148°–149° C. (isopropylalcohol); 1HNMR (DMSO-D$_6$): delta 7.9–7.4 (m, 3H), 6.0 (s, 1H), 2.8 (s, 3H).

2-amino-4-(3-phenyl-5-methyl-4-isoxazolyl)-thiazole, Yield, 69.5%; crystalline compound, m.p. 223°–224° C. (methyl alcohol); 1HNMR (DMSO-d$_6$): delta 7.62 (s, 1H), 6.43 (s, 1H), 2.58 (s, 3H).

(2) 2-amino-4-(3-methoxy-5-isoxazolyl)-thiazole

A mixture of 9.2 g (41.8 mmol) of 3-methoxy-5-bromoacetylisoxazole and 6.36 g (83.6 mmol) of thiourea in 140 ml of methyl alcohol was refluxed for 90 minutes and then cooled for 1 hour with an ice bath.

The precipitate was collected by filtration and added to 120 ml of an 1% solution of sodium hydroxide while stirring vigorously.

The solution was allowed to stand for 30 minutes at room temperature, the precipiate was collected by filtration and washed with water till neutral.

Yield, 6.9 g (83.7%); after recrystallization from methyl alcohol the compound melts at 215°–217° C. 1HNMR (DMSO-d$_6$): delta 7.37 (s, 1H), 6.43 (s, 1H), 4.03 (s, 3H).

In a similar manner was prepared the 1-amino-4-(5-hydroxylmethyl-3-isoxazolyl)-thiazole, Yield, 62.5%; m.p. 185°–187° C. (methyl alcohol); 1HNMR (DMSO-d$_6$): delta 7.3 (s, 1H), 6.7 (s, 1H), 5.7 (t, 1H) 4.6 (d, 2H).

(3) 2-amino-4-(3-chloro-5-isoxazolyl)-thiazole

A mixture of 11.2 g (50 mmol) of 3-chloro-5-bromoacetylisoxazole and 7.6 g (100 mmol) of thiourea in 164 ml of ethyl alcohol was refluxed for 90 minutes and then cooled for 1 hour with an ice bath.

The precipiate was collected by filtration and added to a mixture of 25 ml of a 10% aqueous solution of sodium hydroxide and 100 ml of ethyl acetate under vigorous stirring.

The organic layer was separated, washed, dried and evaporated to dryness. Yield, 7.7 g (77%); after recrystallization from acetonitrile the compound melts at 169°–170° C. 1HNMR (DMSO-d$_6$): delta 7.4 (s, 1H), 6.9 (s, 1H).

In a similar manner the following compounds were prepared:

2-amino-4-(3-benzyloxy-5-isoxazolyl)-thiazole, Yield, 76.5%; m.p. 129°–131° C. (acetonitrile); 1HNMR (CDCl$_3$): delta 7.3 (s, 1H), 6.5 (s, 1H), 5.4 (s, 2H).

2-amino-4-(5-phenyl-3-isoxazolyl)-thiazole, (from 5-phenyl-3-bromoacetylisoxazole, J. Med. Chem. 10, 411, 1967). Yield, 74.5%; m.p. 215°–216° C. (methyl alcohol). Anal: S=12.98% (Calcd. 13.18%)

2-amino-4-(3-phenyl-5-isoxazolyl)-thiazole, (from 3-phenyl-5-bromoacetylisoxazole, J. Med. Chem. 10, 411, 1967). Yield, 65.5%; m.p. 192°–193° C. (acetonitrile). Anal.: S=13.39% (Calcd. 13.18%)

2-amino-4-[3-(2-chloro-6-fluorophenyl)-5-isoxazolyl]-thiazole, Yield, 56.6%; m.p. 168°–169° C. (acetonitrile); Anal: S=11.03% (Calcd. 10.84%).

2-amino-4-(3-methyl-5-isoxazolyl)-thiazole, Yield, 57%; m.p. 208°–210° C. (acetonitrile); 1HNMR (DMSO-d$_6$): delta 7.03 (s, 1H), 6.5 (s, 1H), 2.3 (s, 3H).

2-amino-4-(3-methoxymethyl-5-isoxazolyl)-thiazole, Yield, 49%; m.p. 137°–138° C. (acetonitrile); 1HNMR (DMSO-d$_6$): delta 7.3 (s, 1H), 6.6 (s, 1H), 4.5 (s, 2H), 3.4 (s, 3H).

2-amino-4-(3-bromo-5-isoxazolyl)-5-ethylthiazole, Yield, 70%; m.p. 151°–152° C. (acetonitrile);

1HNMR (DMSO-d$_6$): delta 6.8 (s, 1H), 3.0 (q, 2H), 1.2 (t, 3H).

(4) 2-amino-4-(3-hydroxymethyl-5-isoxazolyl)-thiazole 4.4 g (116.2 mmol) of sodium boron hydride were added portionwise to a solution of 13.9 g (58.1 mmol) of 2-amino-4-(3-carbethoxy-5-isoxazolyl)-thiazole in 40 ml of dimethyl formamide and 80 ml of methyl alcohol under stirring at about 35° C.

When the addition was over, the reaction mixture was stirred at room temperature for 90 minutes and then was made acid by adding carefully 60 ml of 10% hydrochloric acid.

The reaction mixture was evaporated under reduced pressure, the residue was taken up with water and made alkaline with potassium carbonate.

The precipitate was collected by filtration and washed with water. Yield, 11.1 g (97%); m.p. 184°–185° C. (acetonitrile). 1HNMR (DMSO-d$_6$): delta 7.4 (s, 1H), 6.6 (s, 1H), 4.6 (d, 2H).

(5) 2-amino-4-(3-carbethoxy-5-isoxazolyl)-thiazole

A solution of 54.8 g (209 mmol) of 3-carbethoxy-5-bromoacetylisoxazole and 31.8 g (418 mmol) of thiourea in 685 ml of ethanol was refluxed for 90 minutes and then cooled for 1 hour with an ice bath.

The precipitate was collected by filtration and added to an aqueous solution of potassium bicarbonate under vigorous stirring.

The reaction mixture was shaken with ethyl acetate. The combined organic extracts were washed with water, dried and evaporated. Yield, 43.4 g (86.7%); m.p. 156°–157° C. (acetonitrile). 1HNMR (DMSO-d$_6$): delta 7.4 (s, 1H), 7.0 (s, 1H), 4.4 (d, 2H), 1.4 (t, 3H).

(6) 2-amino-4-(3-hydroxy-5-isoxazolyl)-thiazole hydrobromide

A mixture of 13.5 g (68.5 mmol) of 2-amino-4-(3-methoxy-5-isoxazolyl)-2-thiazol and 135 ml of 48% hydrobromic acid was heated while stirring with an outer bath at 100° C. for one hour.

After cooling with a water/ice bath the precipitate was collected by filtration under reduced pressure and dried.

13.3 g (73.6%) of a white crystalline compound were obtained which were purified by crystallization from 1% hydrobromic acid. 1HNMR (DMSO-d$_6$): delta 7.5 (s, 1H); 6.6 (s, 1H).

EXAMPLE E (1) Ethyl 4-(3-bromo-5-isoxazolyl)-thiazole-2-oxamate

To a mixture of 7.38 g (30 mmol) of 4-(3-bromo-5-isoxazolyl-2-thiazolamine and 3.50 g (34.6 mmol) of triethylamine in 60 ml of pyridine, stirred at a temperature not above 10° C. were added dropwise 4.71 g (34.5 mmol) of ethoxalyl chloride.

At the end of the addition the solution was stirred overnight and then diluted with 120 ml of water.

The precipitate was collected by filtration and washed on the filter with abundant water.

After vacuum drying at 50° C. the compound was recrystallized two times from 110 ml and 130 ml of acetonitrile respectively to give 6.90 g of a crystalline compound analitically pure; m.p. 196.5°–197° C. 1HNMR (DMSO)-d$_6$): delta 8.20 (s, 1H); 7.20 (s, 1H); 4.42 (q, 2H,); 1.40 (t, 3H).

In a similar manner was prepared the following compound:

Ethyl-4-(3-phenyl-5-methyl-4-isoxazolyl)-thiazole-2-oxamate, Yield, 78%; m.p. 157°–159° C. (acetonitrile); 1HNMR (DMSO-d$_6$): delta 7.6 (m, 5H), 7.3 (s, 1H), 3.2 (q, 2H), 2.6 (s, 3H), 1.3 (s, 3H).

(2) Ethyl 4-(3-methoxy-5-isoxazolyl)-thiazole-2-oxamate

To a mixture of 6.60 g (33.5 mmol) of 2-amino-4-(3-metoxy-5-isoxazolyl)-thiazole in 67 ml of pyridine while stirring at 5°–10° C. were added dropwise 5.25 g (38.5 mmol) of ethoxalyl chloride.

The reaction mixture was maintained under stirring overnight, then poured into 120 g of crushed ice and made acid with concentrate hydrochloric acid.

The mixture was extracted wih 750 ml of 1,2-dichloroethane, the organic layer was separated and washed with water.

The organic extracts were evaporated; Yield, 9.40 g (94.5%); m.p. 204°–205° C.; 1HNMR (DMSO-d$_6$): delta 8.10 (s, 1H), 6.6 (s, 1H), 4.4 (q, 2H), 4.0 (s, 3H), 1.4 (t, 3H).

In a similar manner were prepared the following compounds:

Ethyl 4-(5-phenyl-3-isoxazoly)-thiazole-2-oxamate, Yield, 47%; m.p. 169°–170° C. (ethyl alcohol); 1HNMR (DMSO-d$_6$): delta 8.2–7.4 (m, 5H), 8.1 (s, 1H), 7.5 (s, 1H), 4.4 (q, 2H), 1.4 (t, 3H).

Ethyl 4-(3-ethoxalyloxymethyl-5-isoxazolyl)-thiazole-2-oxamate, Yield, 68%; m.p. 150°–151° C. (ethyl alcohol); 1HNMR (DMSO-d$_6$): delta 8.1 (s, 1H), 7.0 (s, 1H), 5.5 (s, 2H), 4.4 (q, 4H), 1.4 (t, 6H).

Benzyl 4-[3-(2-chloro-6-fluorophenyl-5-isoxazolyl]-thiazole-2-oxamate, Yield, 67% m.p. 199°–200° C. (acetonitrile); 1HNMR (DMSO-d$_6$): delta 8.3 (s, 1H), 7.5 (m, 8H), 7.2 (s, 1H), 5.5 (s, 2H).

Cyclohexyl 4-[3-(2-chloro-6-fluorophenyl)-5-isoxazolyl]-thiazole-2-oxamate, Yield, 74%; m.p. 77°–78° C. (ethyl alcohol); 1HNMR (DMSO-d$_6$): delta 8.2 (s, 1H), 7.6 (m, 3H), 7.1 (s, 1H), 4.9 (m, 1H), 2.2–1.1 (m, 10H).

(3) 2-ethoxyethyl 4-(3-benzyloxy-5-isoxazolyl)-thiazole-2-oxamate.

To a mixture of 5.6 g (20.5 mmol) of 2-amino-4-(3-benzyloxy-5-isoxazolyl)-thiazole in 37.4 ml of pyridine maintained under stirring at 5° C. were added dropwise 4.25 g (23.6 mmol) of 2-ethoxyethyloxalyl chloride.

The reaction mixture was maintained under stirring overnight, then poured into 100 g of crushed ice, made acid with concentrate hydrochloric acid and extracted with chloroform.

The chloroform extracts were washed with water, dried and evaporated to dryness. The residue (8.30 g) was recrystallized from 65 ml of acetonitrile; m.p. 142°–144° C. 1HNMR (DMSO-d$_6$): delta 8.2 (s, 1H), 7.6 (m, 5H), 6.7 (s, 1H), 4.5 (m, 2H), 3.8 (m, 2H), 3.6 (q, 2H), 1.2 (t, 3H).

In a similar manner were obtained the following compounds:

2-ethoxyethyl 4-(5-phenyl-3-isoxazolyl)-thiazole-2-oxamate, Yield, 82%; m.p. 146°–147° C. (acetonitrile); 1HNMR (DMSO-d$_6$): delta 8.1 (s, 1H), 8.1–7.5 (m, 5H), 7.5 (s, 1H), 4.5 (m, 2H), 3 (m, 2H), 3.6 (q, 2H), 1.2 (t, 3H).

2-ethoxyethyl 4-(3-phenyl-5-isoxazolyl)-thiazole-2-oxamate, Yield, 84%; m.p. 146°–147° C. (acetonitrile); 1HNMR (DMSO-d$_6$): delta 8.2 (s, 1H), 8.2–7.4 (m, 5H), 7.4 (s, 1H), 4.5 (m, 2H), 3.8 (m, 2H), 3.6 (q, 2H), 1.2 (t, 3H).

2-ethoxyethyl 4-[3-(2-chloro-6-fluorophenyl)-5-isoxazolyl]-thiazole-2-oxamate. Yield, 87%; m.p. 140°–141° C. (acetonitrile); 1HNMR (DMSO-d$_6$): delta 8.2 (s, 1H), 7.7 (m, 3H), 7.2 (s, 1H), 4.5 (m, 2H), 3.8 (m, 2H), 3.6 (q, 2H), 1.2 (t, 3H).

2-ethoxyethyl 4-[3-(2-chloro-6-fluorophenyl)-5-methyl-4-isoxazolyl]-thiazole-2-oxamate, Yield, 85%; m.p. 47°–58° C. 1HNMR (DMSO-d$_6$): delta 8–7.3 (m, 3H), 6.7 (s, 1H) 4.4 (m, 2H), 3.7 (m, 2H), 3.5 (q, 2H), 2.8 (s, 3H), 1.1 (t, 3H).

2-ethoxyethyl 4-(3-methyl-5-isoxazolyl)-thiazole-2-oxamate, Yield, 91%; m.p. 155°–156° C. (acetonitrile); 1HNMR (DMSO-d$_6$): delta 8.0 (s, 1H), 6.7 (s, 1H), 4.5 (m, 2H), 3.8 (m, 2H), 3.6 (q, 2H), 2.3 (s, 3H), 1.1 (t, 3H).

2-ethoxyethyl 4-(3-carbethoxy-5-isoxazolyl)-thiazole-2-oxamate, Yield, 75%; m.p. 145°–146° C. (acetonitrile); 1HNMR (CDCl$_3$): delta 7.7 (s, 1H), 7.0 (s, 1H), 4.5 (q, 2H), 4.5 (m, 2H), 3.8 (m, 2H), 3.6 (q, 2H), 1.4 (t, 3H), 1.2 (t, 3H).

2-ethoxyethyl 4-(3-methoxymethyl-5-isoxazolyl)-thiazole-2-oxamate, Yield, 86%; m.p. 136°–137° C. (ethyl alcohol); 1HNMR (DMSO-d$_6$): delta 8.1 (s, 1H), 6.8 (s, 1H), 4.6 (s, 2H), 4.4 (m, 2H), 3.7 (m, 2H), 3.6 (q, 2H), 3.4 (s, 3H), 1.2 (t, 3H).

2-ethoxyethyl 4-(5-hydroxymethyl-3-isoxazolyl)-thiazole-2-oxamate, Yield, 58%; m.p. 159°–161° C. (acetonitrile); 1HNMR (DMSO-d$_6$): delta 8.0 (s, 1H), 6.9 (s, 1H), 4.7 (s, 2H), 4.5 (m, 2H), 3.8 (m, 2H), 3.6 (q, 2H), 1.2 (t, 3H).

2-ethoxyethyl 4-(3-hydroxy-5-isoxazolyl)-thiazole-2-oxmate, m.p. 217°–219° C. (acetonitrile); 1HNMR (DMSO-d$_6$); delta 8.00 (s, 1H), 6.37 (s, 1H), 4.43 (m, 2H), 3.73 (m, 2H), 3.53 (q, 2H), 1.13 (t, 3H).

2-ethoxyethyl 4-(3-bromo-5-isoxazolyl)-5-ethyl-thiazole-2-oxamate, Yield, 92%; m.p. 128°–129° C. (acetonitrile); 1HNMR (DMSO-d$_6$): delta 7.0 (s, 1H), 4.4

(m, 2H), 3.7 (m, 2H), 3.5 (q, 2H), 3.1 (q, 2H), 1.3 (t, 3H), 1.1 (t, 3H).

ethoxyethyl 4-(3-bromo-5-isoxazolyl)-thiazole-2-oxamate, Yield, 70%; m.p. 162°–164° C. (acetonitrile); 1HNMR (DMSO-$d_6$): delta 8.2 (s, 1H), 7.1 (s, 1H), 4.5 (m, 2H), 3.8 (m, 2H), 3.6 (q, 2H), 1.18 (t, 3H).

2-ethoxyethyl 4-(3-chloro-5-isoxazolyl)-thiazole-2-oxamate, Yield, 81%; m.p. 154°–156° C. (acetonitrile); 1HNMR (DMSO-$d_6$): delta 8.2 (s, 1H), 7.1 (s, 1H), 4.5 (m, 2H), 3.8 (m, 2H), 3.6 (q, 2H), 1.2 (t, 3H).

2-ethoxyethyl 4-(3-methoxy-5-isoxazolyl)-thiazole-2-oxamate, Yield, 78%; m.p. 142°–143° C. (acetonitrile); 1HNMR (DMSO-$d_6$): delta 8.10 (s, 1H), 6.58 (s, 1H), 4.5 (m, 2H), 4.02 (s, 3H), 3.8 (m, 2H), 3.60 (q, 2H), 1.18 (t, 3H).

2-ethoxyethyl 4-(3-phenyl-5-methyl-4-isoxazolyl)-thiazole-2-oxamate, Yield, 80%; m.p. 113°–115° C. (ethyl alcohol); 1HNMR (DMSO-$d_6$): delta 7.50 (m, 5H), 7.20 (s, 1H), 4.4 (m, 2H), 3.7 (m, 2H), 3.5 (q, 2H), 2.57 (s, 3H), 1.13 (t, 3H).

(4) 2-methoxyethyl 4-(3-bromo-5-isoxazolyl)-thiazole-2-oxamate,

To a mixture of 2.50 g (10 mmol) of 2-amino-4-(bromo-5-isoxazolyl)-2-thiazole and 1.16 g (11.5 mmol) of triethylamine in 20 ml of pyridine stirred continously at a temperature of 5° C. were added dropwise 1.91 g (11.5 mmole) of 2-methoxy-ethyl-oxalyl chloride (prepared by adding 2-methoxy-ethanol to an excess of oxalyl chloride and collecting by distillation of the fraction with b.p. 124°–128° C./90 mmHg). At the end of the addition the solution was stirred for one night and then diluted with 50 ml of water.

The precipitate was collected by filtration under reduced pressure, washed abundantly on the filter with water, and dried under reduced pressure at 50° C. 3.10 of raw material were obtained which were recrystallized twice from acetonitrile to give 2.30 g (61%) of an analytically pure crystalline compound, m.p. 175.5°–177° C.; 1HNMR (DMSO-$d_6$): delta 8.17 (s, 1H); 7.13 (s, 1H); 4.50 (m, 2H,); 3.50 (m, 2H); 3.35 (s, 3H).

EXAMPLE F (1) 4-(3-bromo-5-isoxazolyl)-thiazole-2-oxamic acid

A suspension of 12.60 g (36.4 mmol) of ethyl 4-(3-bromo-5-isoxazolyl)-thiazole-2-oxamate in 500 ml of N/10 sodium hydroxide was stirred at 40° C. for 45 minutes.

The reaction mixture was cooled to room temperature, extracted twice with 150 ml of ethyl ether, treated with active charcoal, and filtered.

The filtrate was acidified with 60 ml of 1N hydrochloric acid and the precipitate was collected by filtration and washed on the filter abundantly with water. 9.80 g (84.5%); m.p. 217°–218.5° C. (dec.). 1HNMR (DMSO-$d_6$): delta 8.13 (s, 1H); 7.16 (s, 1H).

(2) 2-aminoethanol 4-(3-bromo-5-isoxazolyl)-thiazole-2-oxamate salt

A suspension of 2.85 g (8.95 mmol) of 4-(3-bromo-5-isoxazolyl)-thiazole-2-oxamic acid in 25 ml of ethanol was heated on a steam-bath while stirring. To this mixture were added 0.59 g (9.66 mmol) of ethanolamine in 10 ml of ethyl alcohol and 20 ml of water.

The solution was cooled to room temperature and then allowed to stand at 4° C. for one night.

The precipitate was collected by filtration, dried and recrystallized from 65 ml of a 2:1 ethyl alcohol/water mixture. Yield, 2 g (59%); m.p. 190°–193° C. (dec.). 1HNMR (DMSO-$d_6$): 8.0 (s, 1H), 7 (s, 1H), 3.7 (m, 2H), 3.0 (m, 2H).

(3) tromethamine 4-(3-bromo-5-isoxazolyl)-thiazole-2-oxamate salt

To a solution of 3.20 g (26.4 mmol) of tromethamine in 75 ml of methanol, kept under stirring with slight refluxing, were added all at once 8.4 g (26.3 mmole) of 4-(3-bromo-5-isoxazolyl-2-thiazolyl) oxamic acid.

The reaction mixture was cooled to room temperature and after approximately 15 minutes the precipitate was collected by filtration, washed on the filter with cold methanol, and dried.

The crude compound (7.10 g; 61.5%) was recrystalized from methanol; m.p. 183° C. (dec.); 1HNMR (DMSO-$d_6$+$D_2O$): delta 8.07 (s, 1H); 7.17 (s, 1H); 3.65 (s, 6H).

(4) L-lysine 4-(3-bromo-5-isoxazolyl)-thiazole-2-oxamate salt 2.6 g (8.2 mmol) of 4-(3-bromo-5-isoxazolyl)-thiazole-2-oxamic acid were added to a solution of 1.25 g (8.6 mmol) of L-lysine in 140 ml of 75% aqueous ethyl alcohol while refluxing and stirring.

After cooling to 0° C. the mixture was maintained under stirring for 3 hours. The precipitate was collected by filtration; yield, 2.7 g (71%); m.p. 196°–197° C. (dec.); 1HNMR ($D_2O$): delta 7.5 (s, 1H), 6.5 (s, 1H), 3.9 (t, 3H), 3.1 (m, 2H), 2.2–1.3 (m, 6H).

In a similar manner were prepared the following compounds:

4-(3-methoxy-5-isoxazolyl)-thiazole-2-oxamic acid, Yield, 82%; m.p. 224°–225° C. (dec.); 1HNMR (DMSO-$d_6$): delta 8.0 (s, 1H), 6.5 (s, 1H), 4.0 (s, 3H).

2-aminoethanol 4-(3-methoxy-5-isoxazolyl)-thiazole-2-oxamate salt, Yield, 83.7%; m.p. 214°–215° C. dec. (75% ethyl alcohol); 1HNMR (DMSO-$d_6$): delta 7.1 (s, 1H), 6.5 (s, 1H), 4.0 (s, 3H), 3.7 (m, 2H), 3.0 (m, 2H).

2-aminoethanol 4-(3-chloro-5-isoxazolyl)-thiazole-2-oxamate salt, Yield, 71%; m.p. 211° C. dec. (70% ethyl alcohol); 1HNMR (TFAA): delta 8.1 (s, 1H), 7.1 (s, 1H), 3.7 (m, 2H), 3.0 (m, 2H).

2-aminoethanol 4-(5-phenyl-3-isoxazolyl)-thiazole-2-oxamate salt, Yield, 68.5%; m.p. 210°–211° C. dec. (75% methyl alcohol); 1HNMR (DMSO $d_6$): delta 8.2–7.1 (m, 5H), 8.2 (s, 1H), 7.4 (s, 1H), 3.8 (m, 2H), 3.0 (m, 2H).

2-aminoethanol 4-(3-phenyl-5-isoxazolyl)-thiazole-2-oxamate salt, Yield, 73%; m.p. 207°–208° C. dec. (85% ethyl alcohol); 1HNMR (DMSO-$d_6$): delta 9–7.3 (m, 6H), 7.4 (s, 1H), 3.8 (m, 2H), 3.1 (m, 2H).

L-lysine 4-(5-phenyl-3-isoxazolyl)-thiazole-2-oxamate salt, Yield, 64.5%; m.p. 240°–241° C. dec. (20% methyl alcohol); 1HNMR (TFAA): delta 8.1–7.3 (m, 5H), 8.0 (s, 1H), 7.3 (s, 1H), 4.0 (t, 1H), 2.9 (m, 2H), 2.2–1.3 (m, 6H).

2-aminoethanol 4-[3-(2-chloro-6-fluorophenyl)-5-isoxazolyl]-thiazole-2-oxamate salt, Yield, 56%; m.p. 230°–231° C., dec. (70% ethyl alcohol); 1HNMR (DMSO-$d_6$): delta 8.2–7.0 (m, 3H), 8.1 (s, 1H), 7.1 (s, 1H), 3.7 (m, 2H), 3.0 (m, 2H).

4-(3-phenyl-5-methyl-4-isoxazolyl)-thiazole-2-oxamic acid, Yield, 62%; m.p. 187°–188° C., dec. (isopropyl alcohol); 1HNMR (DMSO-$d_6$): delta 7.6 (m, 5H), 7.2 (s, 1H), 2.6 (s, 3H).

2-aminoethanol 4-[3-(2-chloro-6-fluorophenyl)-5-methyl-4-isoxazolyl]-thiazole-2-oxamate salts, Yield, 60%; m.p. 164°-166° C., dec. (isopropyl alcohol); 1HNMR (DMSO, d₆): delta 8-7.3 (m, 3H), 6.6 (s, 1H), 3.7 (m, 2H), 2.9 (m, 2H), 2.8 (s, 3H).

2-aminoethanol 4-(5-hydroxymethyl-3-isoxazolyl)-thiazole-2-oxamate salts, Yield, 61%; m.p. 185°-187° C., dec. (methyl alcohol); 1HNMR (DMSO-d₆): delta 7.9 (s, 1H), 6.8 (s, 1H), 4.6 (s, 2H), 3.7 (m, 2H), 3.0 (m, 2H).

2-aminoethanol 4-(3-hydroxymethyl-5-isoxazolyl)-thiazole-2-oxamate salts, Yield, 69%; m.p. 196°-197° C., dec. (75% methyl alcohol); 1HNMR (DMSO-d₆): delta 7.9 (s, 1H), 6.8 (s, 1H), 4.6 (s, 2H), 3.7 (m, 2H), 3.0 (m, 2H).

(5) Sodium 4-(3-methoxy-5-isoxazolyl)-thiazole-2-oxamate salts

A suspension of 11.9 g (35 mmol) of ethoxyethyl 4-(3-metoxy-5-isoxazolyl)-thiazole-2-oxamate in 500 ml of N/10 sodium hydroxide was stirred at 40° C. for 30 minutes.

After cooling to 0° C., the precipitate was collected by filtration and dried. Yield, 2.4 g (23.5%); m.p. 320° C., dec. 1HNMR (TFAA): delta 8.1 (s, 1H), 6.8 (s, 1H), 4.2 (s, 3H).

EXAMPLE G (1) N-[4-(3-bromo-5-isoxazolyl)-2-thiazolyl]-oxamide

A mixture of 3.50 g (10 mmol) of ethyl 4-(3-bromo-5-isoxazolyl)-thiazole-2-oxamate and 25 ml of a 10% solution of ammonia in methyl alcohol was stirred at room temperature for 24 hours.

The precipitate was collected by filtration, dried under reduced pressure at 50° C. (2.70 g) and recrystallized from 55 ml of glacial acetic acid to give 2.20 g (69%) of analytically pure crystalline product which decomposes without melting at 255° C. 1HNMR (DMSO-d₆): delta 8.20 (s, 1H), 7.20 (s, 1H)

(2) N-[4-(3-methoxy-5-isoxazolyl)-2-thiazolyl]-oxamide

A mixture of 8.6 g (28.9 mmol) of ethyl 4-(3-methoxy-5-isoxazolyl)-thiazole-2-oxamate in 143 ml of a 16% ammonium hydroxide solution in methyl alcohol was stirred overnight at room temperature.

The solvent was evaporated and the residue (7.5 g) was recrystallized from 220 ml of glacial acetic acid. Yield, 6.2 g (80%); crystalline compound which decomposes at 250° C. without melting. 1HNMR (DMSO-d₆): delta 8.0 (s, 1H), 6.5 (s, 1H), 4.0 (s, 3H).

In a similar manner were prepared the following compounds:

N-[4-(3-phenyl-5-methyl-4-isoxazolyl)-2-thiazolyl]-oxamide, Yield, 73%; m.p. 204°-205° C. (acetonitrile); 1HNMR (DMSO-d₆): delta 7.6 (m, 5H), 7.2 (s, 1H), 2.6 (s, 3H).

N-[4-(5-phenyl-3-isoxazolyl)-2-thiazolyl]-oxamide, Yield, 74%; m.p. 246°-247° C. (glacial acetic acid); 1HNMR (DMSO-d₆): delta 8.2-7.4 (m, 5H), 8.1 (s, H), 7.5 (s, 1H).

N-[(4-(2-chloro-6-fluorophenyl)-5-isoxazolyl)-2-thiazolyl]-oxamide, Yield, 77%, m.p. 235°-237° C. (glacial acetic acid); 1HNMR (DMSO-d₆): delta 8.2 (s, 1H), 7.6 (m, 3H), 7.2 (s, 1H).

N[4-(3-methyl-5-isoxazolyl)-2-thiazolyl]-oxamide, Yield, 90%; m.p. 245°-246° C. (glacial acetic acid); 1HNMR (DMSO-d₆): delta 8.0 (s, 1H), 6.7 (s, 1H), 3.3 (s, 3H).

N-[4-(3-bromo-5-isoxazolyl)-5-ethyl-2-thiazolyl]-oxamide, Yield, 85%; 210°-221° C., dec. (glacial acetic acid); 1HNMR (DMSO-d₆): delta 7.0 (s, 1H), 3.1 (q, 2H), 1.3 (t, 3H).

N-[4-(3-hydroxymethyl-5-isoxazolyl)-2-thiazolyl]-oxamide, Yield, 45%, 250°-255° C., dec. (glacial acetic acid); 1HNMR (DMSO-d₆): delta 8.0 (s, 1H), 6.8 (s, 1H), 4.6 (s, 2H).

(3) 1-[4-(3-bromo-5-isoxazolyl)-thiazole-2-oxamoyl]-4-methyl-pyperazine

A mixture of 7.3 g (21.1 mmol) of ethyl 4-(3-bromo-5-isoxazolyl)-thiazole-2-oxamate and 36.5 ml of N-methyl-pyperazine was stirred overnight at room temperature.

The solution was then poured into 350 ml of isopropyl ether while stirring, the precipitate was collected by filtration and taken up with hot methyl alcohol.

The suspension was refluxed and stirred for 30 minutes, and then cooled to 0° C. and filtered.

The residual of the filtration was dissolved at 100° C. in 80 ml of dimethylformamide. The solution was cooled to 0° C., the precipitate was collected by filtration and dried. Yield, 3.5 g (41.5%) of a crystalline compound which melts slowly at 200° C.; 1HNMR (TFAA): delta 8.1 (s, 1H), 7.2 (s, 1H), 4.2-3.2 (m, 8H), 3.2 (s, 3H).

(4) N,N'-bis-[4-(3-bromo-5-isoxazolyl)-2-thiazolyl]-oxamide

To a solution of 10.1 g (41 mmol) of 2-amino-4-(3-bromo-5-isoxazolyl)-thiazole in 160 ml of 1,2-dichloroethane were added 4.13 g (41 mmol) of triethylamine in 15 ml of 1,2-dichloroethane.

The mixture was heated to 60° C. and stirred; a solution of 2.60 (20.5 mmol) of oxalyl chloride in 15 ml of 1,2-dichloromethane was added slowly dropwise.

The thus obtained mixture was stirred overnight at room temperature. The precipitate was collected by filtration and washed with methyl alcohol.

The crude product (5.8 g) was recrystallized from 195 ml of tetrahydrofuran. Yield, 4.5 g (40%) of a crystalline compound which decomposes slowly at 280° C. 1HNMR (DMSO-d₆): delta 8.1 (s, 1H), 7.1 (s, 1H).

(5) N-[4-(3-bromo-5-isoxazolyl)-2-thiazolyl]-N'-isopropyl-oxamide

A solution of 7.1 g (20.5 mmol) of ethyl 4-(3-bromo-5-isoxazolyl)-thiazole-2-oxamate in 30 ml of isopropylamine was stirred overnight at room temperature.

The solvent was removed by evaporation and the residue was crystallized from 300 ml of methyl alcohol. Yield, 3.2 g (43.5%); m.p. 194°-195° C.; 1HNMR (DMSO-d₆): delta 8.1 (s, 1H), 7.1 (s, 1H), 7.1 (s, 1H), 4.1 (m, 1H), 1.2 (d, 6H).

What is claimed:

1. A compound of formula:

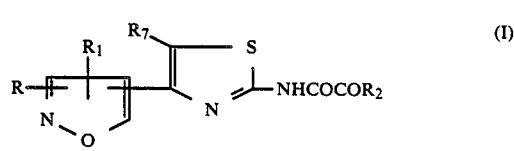

wherein

R and $R_1$ which may be the same or different represent a hydroxy group; a hydrogen or halogen atom; a $C_1$-$C_6$ alkyl or alkoxy group optionally substituted by from one to three substituents selected from the group consisting of halogen, hydroxy, alkoxy, amino, carboxy, alkoxycarbonyl, alkoxalyloxy, and phenyl, the latter in turn optionally substituted by from one to three substituents selected from the group consisting of halogen, hydroxy, alkoxy, amino and trifluoroalkyl; a phenyl group optionally substituted by from one to three substituents selected from the group consisting of halogen, hydroxy, alkoxy, amino and trifluoromethyl;

$R_2$ is a hydroxy group, an $OR_3$ group or an $NR_4R_5$ group;

$R_3$ is a $C_1$-$C_6$ alkyl group optionally substituted with from one to three substituents selected from the group consisting of hydroxy, alkoxy, amino, carboxy and alkoxycarbonyl; a $C_{5-6}$ cycloalkyl group optionally substituted by from one to three alkyl groups; a $C_7$-$C_9$ phenylalkyl group optionally substituted on the phenyl ring by from one to three substituents selected from the group consisting of halogen, methyl and methoxy group; a group of the formula —$(CH_2-CH_2-O)_n$—$R_6$ wherein n is an integer number of 2 to 4 and $R_6$ is a hydrogen atom or an alkyl group;

$R_4$ and $R_5$ which may be the same or different are a hydrogen atom, an alkyl, a $C_5$-$C_6$ cycloalkyl, a $C_7$-$C_9$ phenylalkyl or a phenyl group; or $R_4$ and $R_5$ together with the nitrogen atom to which they are linked, form a 1-piperidyl, 1-piperazinyl, 4-methyl-1-piperazinyl, pirazolyl thiazolyl or imidazolyl radical; or either $R_4$ or $R_5$ is a hydrogen atom and the other a group of the formula

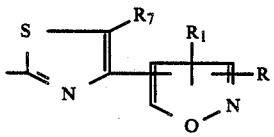

wherein
R and $R_1$ have the above indicated meanings;
$R_7$ is a hydrogen atom or a $C_1$-$C_3$ alkyl radical;

and pharmaceutically acceptable salts thereof with organic and inorganic bases when $R_2$ is a hydroxy group and with organic and inorganic acids when $R_2$ contains a basic function;

with the proviso that $R_2$ is not a hydroxy group or an $OR_3$ group when the isoxazolyl radical is a 3- or a 5-isoxazolyl radical.

2. A compound according to claim 1, wherein R and $R_1$ are each independently hydrogen, chlorine, bromine, hydroxy, methyl, methoxy, ethoxy, benzyloxy, phenyl, halosubstituted phenyl, hydroxymethyl, methoxymethyl, ethoxymethyl or carbethoxy; $R_2$ is a hydroxy group, an $OR_3$ or $NR_4R_5$ group where in turn $R_3$ is ethoxyethyl, ethyl, cyclohexyl or phenylmethyl; $R_4$ and $R_5$ are each independently hydrogen, $C_{1-4}$ alkyl or a bromo-isoxazolyl-thiazole group; $R_4$ and $R_5$ together with the nitrogen atom to which they are linked form a 4-methyl-pyperazinyl group.

3. N-[4-(3-bromo-5-isoxazolyl)-2-thiazolyl]-oxamide.

4. N,N'-[4-(3-bromo-5-isoxazolyl)-2-thiazolyl]-oxamide.

5. A pharmaceutical composition having antiarthritic activity and containing an effective amount for the purpose of a compound according to claims 1 or 2 or 3 or 4.

6. Method of treating a subject having symptoms of arthritis comprising administering to such subject a pharmaceutical composition having antiarthritic activity wherein the active ingredient is present, in an effective amount for the purpose, of a compound according to claim 1 or 2 or 3 or 4.

7. A compound of formula

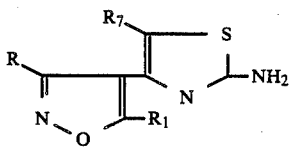

wherein
R and $R_1$ are each independently hydrogen, chlorine, bromine, hydroxy, methyl, methoxy, ethoxy, benzyloxy, phenyl, halo substituted phenyl, hydroxymethyl, methoxymethyl, ethoxymethyl or carbethoxy; and
$R_7$ is hydrogen or $C_{1-3}$ alkyl.

* * * * *